United States Patent [19]

Wildenauer

[11] Patent Number: 4,758,344

[45] Date of Patent: Jul. 19, 1988

[54] METHOD FOR TREATING ORGANIC GARBAGE, ESPECIALLY HOUSEHOLD REFUSE

[75] Inventor: Franz X. Wildenauer, Munich, Fed. Rep. of Germany

[73] Assignee: Messerschmitt-Boelkow-Blohm GmbH, Munich, Fed. Rep. of Germany

[21] Appl. No.: 942,265

[22] Filed: Dec. 17, 1986

[30] Foreign Application Priority Data

Dec. 21, 1985 [DE] Fed. Rep. of Germany ....... 3545679

[51] Int. Cl.$^4$ .......................... C02F 3/28; C05F 9/04
[52] U.S. Cl. .................................. 210/603; 210/617; 210/630; 210/717; 210/912; 71/9; 71/14
[58] Field of Search ............... 210/603, 617, 630, 717, 210/912, 913, 914; 71/9, 14, 901

[56] References Cited

U.S. PATENT DOCUMENTS

| | | | |
|---|---|---|---|
| 1,029,378 | 6/1912 | Lawton | 71/9 |
| 3,241,943 | 3/1966 | Bystrom | 71/9 |
| 4,302,236 | 11/1981 | Roman | 71/9 |
| 4,342,650 | 8/1982 | Erickson | 210/912 |
| 4,504,394 | 3/1985 | Breuer | 210/912 |
| 4,565,633 | 1/1986 | Mayenkar | 210/912 |

Primary Examiner—Ernest G. Therkorn
Attorney, Agent, or Firm—W. G. Fasse; D. H. Kane, Jr.

[57] ABSTRACT

Organic waste, especially organic household garbage, is leached in a leaching apparatus for washing out any water soluble organic substances and water soluble heavy metal salts. Air is supplied into the apparatus during the leaching for aerobically decomposing or rotting the organic substances. Non-soluble substances are discharged from the leaching apparatus for further treatment. A liquid flow-off component containing solved substances is withdrawn from the leaching apparatus, collected in an intermediate tank and introduced into an anaerobic solid bed reactor wherein anaerobic bacteria reduce or decompose the liquid flow-off component to form bio-gas which is withdrawn from the solid bed reactor for use or storage in a low pressure tank. The heavy metal salts are precipitated into water non-soluble sulfides and the flow-off is returned for further leaching to the leaching apparatus in a substantially closed circuit in which any lost leaching liquid is replenished.

9 Claims, 1 Drawing Sheet

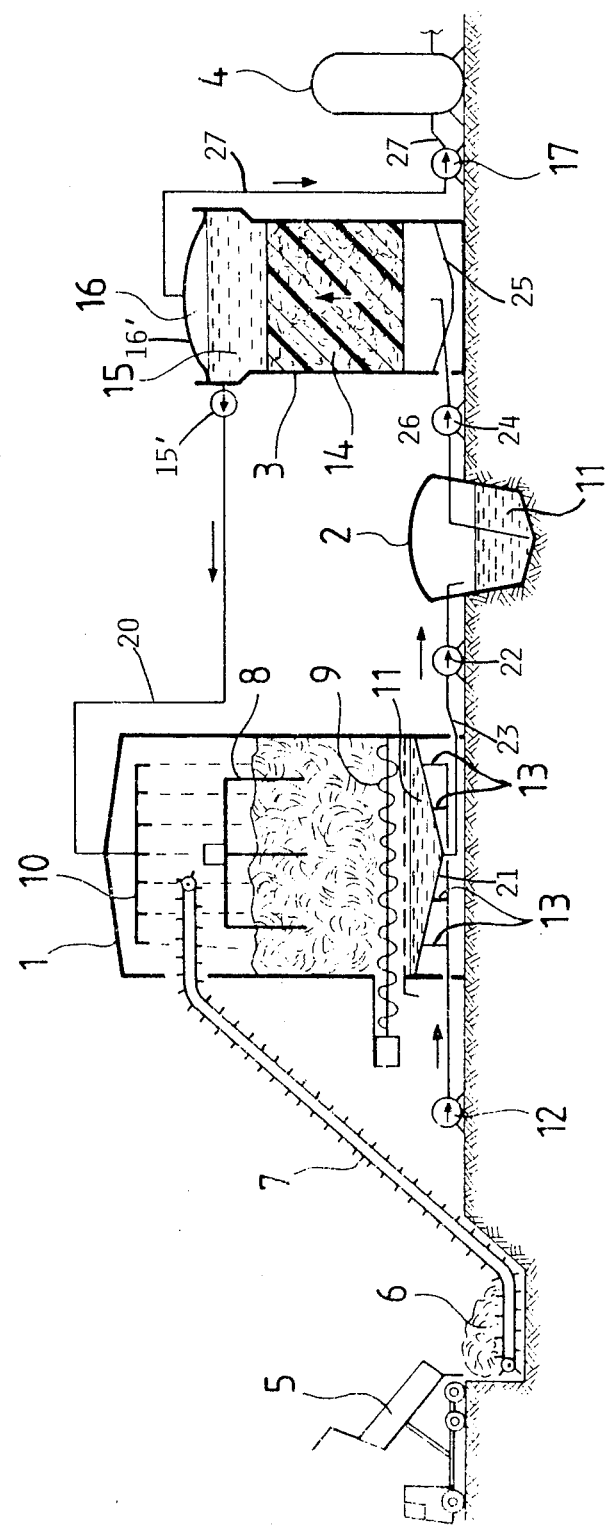

METHOD FOR TREATING ORGANIC GARBAGE, ESPECIALLY HOUSEHOLD REFUSE

FIELD OF THE INVENTION

The invention relates to a method for treating organic garbage, especially organic household waste which normally comprises heavy metal salts, and which was presorted for removing any inorganic components. Biochemical processes are employed in the present treatment operation.

DESCRIPTION OF THE PRIOR ART

Household garbage comprises on the average about 35 to 50% of organic substances. These organic substances may be separated by conventional presorting methods from the other garbage components. Ecologic problems occur in the removal of toxic heavy metal compounds which are present, as a rule, in the organic household garbage substances.

For example, in the Federal Republic of Germany the annual "production" of household garbage amounts to about 15 million tons which heretofore have been deposited to a substantial extent in about 530 controlled garbage dumps or pyrolytically decomposed in garbage incinerating plants. Where garbage is simply placed into garbage dumps, there is the danger that the mentioned heavy metal compounds will be washed out by rain and eventually enter into the ground water. On the other hand, where incineration of garbage is employed, there is the danger that the toxic compounds contribute to the further air contamination. Another disadvantage of dumping garbage is the need for very much space. Additionally, there is no energy recovery possible from a garbage dump.

Another conventional method which, however, is used only in about 3% of the number of households involves treating the organic refuse or waste by composting. For this purpose the garbage is presorted and the easily decomposing organic substances are subjected to a rotting process while simultaneously oxygen is being supplied and heat is generated due to an oxidation. As a result of the composting, a final product is obtained which is more hygienic and which has a noticeably smaller volume. To this extent the composting is an effective measure for reducing the garbage or refuse volume. However, the composting method as such is unable to remove environmentally harmful components such as heavy metals from the compost. The fact that the compost contains heavy metals militates against its use, for example, as a soil improvement in agriculture.

Based on the fact that more than 60% of the entire household garbage or refuse is made up of biologically decomposable cellulose in the form of foodstuff leftovers, paper, and cardboard, attempts have been made to subject the organic waste components to an anaerobic decomposition with or without sedimentation. The purpose of such treatment is to obtain, in addition to the biological stabilization, energy in the form of methane gas. However, due to the fact that certain organic substances are not or hardly decomposable by an anaerobic process, conventional reactor structures have encountered substantial mixing problems caused by floating covers or by sediment formation. These difficulties with prior art anaerobic reactors made an economic or rather efficient operation impossible as far as the generation of useful bio-gas is concerned.

In this context it is also known that anaerobic reactors are suitable for retaining heavy metals such as zinc, copper, chromium, nickel, lead, mercury, and cobalt. This ability of conventional anaerobic reactors will retain up to 90% of the heavy metals by the formation of non-soluble metal sulfides.

OBJECTS OF THE INVENTION

In view of the foregoing it is the aim of the invention to achieve the following objects singly or in combination:

to provide a method for the efficient treatment of organic garbage or refuse components, especially household garbage obtained by a presorting operation;

to provide a method for a garbage treatment in which a continuous process will result in a significant or noticeable volume reduction;

to cause a controlled precipitation of heavy metal compounds especially in an anaerobic treatment tower;

to provide an economically feasible energy recovery in the form of a bio-gas comprising the energy containing methane; and to perform the treatment in a substantially uninterrupted circuit in which any water or leaching liquid losses are replenished, either continuously or in batch type liquid additions.

SUMMARY OF THE INVENTION

The garbage treatment method according to the invention is characterized by the following steps. The organic refuse or organic waste substances are introduced into and uniformly distributed in a leaching device or apparatus such as a leaching tower. A leaching liquid which is primarily water is introduced into the leaching tower for washing out any water soluble organic substances and any water soluble heavy metal salts from the organic garbage substances. A controlled air flow is introduced into the tower, for example, through air nozzles, for the aerobic rotting of the organic substances during the leaching. Any substances that are in-soluble are removed from the leaching apparatus for further treatment, for example, dumping. The removal is performed, for example, with a conveyor such as a scraping or screw conveyor. The leaching liquid containing the solved substances is withdrawn from the leaching apparatus and stored in an intermediate tank from which the leaching liquid is in turn withdrawn as needed for supply into an anaerobic solid bed reactor. The withdrawn leaching liquid is also referred to as the liquid flow-off from the tower. The organic substances solved in the liquid flow-off are decomposed or reduced in the solid bed reactor to form a so-called bio-gas containing methane and carbon dioxide, whereby the reducing or decomposing is caused by the action of anaerobic bacteria in the solid bed of the reactor. The heavy metal compounds are also precipitated in the solid bed reactor with the aid of sulfur containing substances to form water non-soluble heavy metal sulfides. The liquid overflow from the solid bed reactor is returned into the leaching apparatus for wetting the organic refuse, whereby a substantially continuous circuit operation is achieved. However, any loss of leaching liquid is replenished, either continuously or in a batch type supply operation. The bio-gas is withdrawn from the solid bed reactor for further use, for example, as a fuel.

Thus, the invention combines substantially three methods, namely the leaching, the composting or rotting, and the methane formation. The two first steps take place simultaneously in the same space, namely in the leaching tower under aerobic conditions. The anaerobic third step takes place in the separate solid bed reactor and subsequent to the first two steps. The volume of the organic refuse is substantially or noticeably reduced by the aerobic rotting. The leaching operation washes those substances out of the organic refuse which are most suitable for the methane generation while also washing out the heavy metal compounds so that it now becomes possible to use the compost coming out of the leaching tower as an agricultural fertilizer or it can be dumped without any problems because the leaching has detoxified the substantially solid compost so that rain water cannot wash heavy metals into the ground water.

The removal of the solid substances from the leaching tower is an important condition for an operation of the solid bed reactor without any problems.

The intermediate tank for temporarily taking up the liquid flow-off, serves for the purpose to decouple the methane generation in the solid bed reactor from the processes taking place in the leaching apparatus since these processes in the leaching apparatus are partially non-stationary. The solid bed reactor performs two functions, namely it facilitates the energy recovery in the form of bio-gas and thus methane generation and it also facilitates the precipitation of the heavy metals in the form of water non-soluble sulfides which thus may be removed in a controlled manner for any further treatment if desired. It is estimated that an efficient embodiment of the apparatus for practicing the present invention will yield more energy in the recovered methane than is necessary for operating the system.

BRIEF DESCRIPTION OF THE DRAWING

In order that the invention may be clearly understood, it will now be described, by way of example, with reference to the single figure of the accompanying drawing, showing, partially in section, a schematic side view of a system for performing the method according to the invention.

DETAILED DESCRIPTION OF A PREFERRED EXAMPLE EMBODIMENT AND OF THE BEST MODE OF THE INVENTION

A dump truck 5 shown at the left-hand end of the drawing supplies the presorted organic garbage or refuse substances, especially organic household refuse 6 onto a conveyor 7 which feeds the refuse 6 into a leaching tower 1. It is preferable that the organic refuse 6 is comminuted after inorganic garbage components such as solid metals and other inorganic substances have been removed, but prior to feeding the garbage 6 into the leaching tower 1. The conveyor 7 may, for example, be a scraping chain conveyor, a bucket conveyor or any other conveyor device suitable for feeding the garbage 6 into the top portion of the tower 1. The tower 1 is equipped with a motor driven distributor 8 of conventional construction, for uniformly distributing the garbage in the tower. Watering pipes 10 with a plurality of spray openings are provided for supplying a leaching liquid into the tower. The leaching liquid is primarily water supplied from an overflow 15 in a solid bed reactor 3. The leaching liquid is pumped by a pump 15' through a conduit 20 into the pipes 10 in the top of the tower 1.

The watery leaching liquid supplied into the top of the tower 1 washes the water soluble organic substances and the water soluble heavy metal salts out of the refuse 6 in the tower 1, wherein the leaching liquid is collected in a bottom trough 21 provided with a plurality of air blowing nozzles 13 connected to a compressor 12 for supplying air into the leaching tower 1 to facilitate the aerobic action inside the leaching tower 1. With the aid of the air the water non-soluble organic substances in the tower are oxidized, whereby these non-water soluble organic substances become hygienically acceptable and whereby their volume is reduced.

The speed of the aerobic composting process in the leaching tower can be controlled by regulating the volume of the compressed air flow into the trough 21 of the tower 1.

The composted organic material is removed from the tower 1 by conveying means 9 which may be a screw conveyor or the like of conventional construction. The output of the conveyor 9 may be moved, for example, to a dump or it may be used as fertilizer, for example.

Any liquid that is lost in the tower 10 due to the removal of compost is replenished into the otherwise substantially closed circuit. The replenishing may take place continuously or in a batch type operation, for example, by connecting the watering pipes 10 to a water supply in addition to the conduit 20.

The liquid flow-off 11 from the trough 21 is supplied by a pump 22 through a conduit 23 into an intermediate tank 2. A further pump 24 between the tank 2 and the bottom 25 of the solid bed reactor 3 is used for controlling the supply of the liquid flow-off 11 into the solid bed reactor 3 through a conduit 26. By collecting the liquid flow-off 11 in the intermediate tank 2 it is possible to control the quantity of liquid supplied into the reactor 3 in accordance with the requirements of the reactor 3 and to decouple the aerobic action in the leaching tower 1 from the anaerobic action in the reactor 3.

The reactor 3 is equipped with a porous solid bed 14, for example, made of plastic-pall rings or clay-tubes of 60 mm in diameter through which the liquid can flow from the bottom up under the pressure of the pump 24. Anaerobic bacteria act in the solid bed 14 for converting the solved organic substances into carbon dioxide and methane, thereby forming bio-gas which is collected in the space 16 below the cover 16' of the reactor 3. The vaulted cover 16' floats on the liquid in the overflow 15 of the reactor 3. A pump 17 connected by a conduit 27 through the cover 16' and to a low pressure storage tank 4, transports the bio-gas into the container 4 for further use, for example as a fuel. The reducing atmosphere in the solid bed reactor 3 and the presence of $H_2S$ from the bacterial breakdown of solved protein converts the heavy metal salts in solution in the liquid into water non-soluble sulfides which are precipitated as solids for removal from the liquid. Such removal of the solid sulfides from the leaching liquid circuit can be performed selectively, for example. The metal sulfides will accumulate in the bio-mass sludge on the bottom of the reactor 3. The sludge can be withdrawn by pumping when necessary.

The removed sulfides can be further treated or deposited in places provided for this purpose.

Due to the described continuous circuit flow of the leaching liquid, it is possible to minimize the water consumption of the system since only the relatively small liquid proportion needs to be replaced that remains in the compost removed by the conveyor 9.

In an example embodiment the leaching tower 1 may have a volume of about 500 cubic meter and operates at atmospheric pressure in a temperature range of about 40° C. to about 60° C., the respective heat being provided by the composting action. Any aerobic bacteria suitable for the composting may be used. The refuse 6 should be comminuted to pieces not exceeding about 50 mm in length and/or diameter. Sizes within the range of 10 to 60 mm mesh-size are suitable. About 25 cubic meter of such a comminuted refuse may be fed into the tower 1 per day. The air supply into the tower 1 will depend on the type of refuse being treated and will typically be within the range of about 0 to 5 cubic meter of air per cubic meter of tower volume per hour.

The decoupling container 2 has, for example, a volume of about 20 cubic meter and operates at atmospheric pressure in a temperature range of about 10° C. to about 20° C. The solid bed reactor 3 has, for example, a volume of 100 cubic meter, operates at a pressure of about 10 millibar (gage) and at a temperature of about 350° C. About 10 to 30 cubic meter of flow-off 11 may be supplied per day into the solid bed reactor 3. The low pressure methane container 4 is maintained at about 10 millibar (gage) and has, for example, a volume of about 20 cubic meter.

Bacteria suitable for the anaerobic reaction in the solid bed reactor 3 may, for example, be Clostridium, Bacteroidaceae, Eubacterium, Desulfovibrio, Methanosarcina, Methanobacterium, or Methanococcus.

The leaching liquid is primarily water containing about 2% by volume of dry substance. About 1.8% of said 2% are organic dry substances.

Although the invention has been described with reference to specific example embodiments, it will be appreciated that it is intended to cover all modifications and equivalents within the scope of the appended claims.

What I claim is:

1. A method for treating organic waste material normally including heavy metal salts, comprising the following steps:
   (a) introducing the organic waste material into a leaching device,
   (b) uniformly distributing the organic waste material within the leaching device,
   (c) leaching said organic material by a leaching liquid including primarily water in said leaching device for washing soluble substances including heavy metal salts out of said organic waste material to provide a liquid flow-off component comprising said soluble substances including said heavy metal salts in solution,
   (d) aerobic rotting of the organic material by introducing air into said leaching device during said leaching step,
   (e) removal of non-soluble substances from the leaching device for further treatment,
   (f) withdrawal of said liquid flow-off component containing solved substances, from the leaching device,
   (g) collecting, in an intermediate tank, said liquid flow-off component containing said solved substances,
   (h) withdrawing said liquid flow-off component from said intermediate tank as needed,
   (i) introducing said liquid flow-off component into an anaerobic solid bed reactor,
   (j) reducing said solved organic substances in said solid bed reactor, into a bio-gas containing methane gas and carbon dioxide by subjecting said solved organic substances in said solid bed reactor to the action of anaerobic bacteria,
   (k) precipitating said heavy metal salts by a reaction for forming non-soluble heavy metal sulfides,
   (l) returning a liquid overflow from said solid bed reactor to said leaching device for supplying said leaching liquid to said leaching device for irrigating said organic waste material in a leaching circuit, and
   (m) withdrawing said bio-gas from said solid bed reactor for further use.

2. The method of claim 1, wherein said step of introducing involves loading said organic waste material into a top of said leaching device, wherein said steps of leaching and aerobic rotting are performed in a substantially closed leaching device under atmospheric pressure, wherein said leaching step is performed by spraying or irrigating leaching liquid from above onto said organic waste material, wherein said aerobic rotting step involves blowing compressed air through a bottom into said leaching device, wherein said removal step is performed by removing layers at the bottom of said leaching device, and wherein said withdrawing step of said liquid flow-off component is performed at a lowest point in said leaching device.

3. The method of claim 1, further comprising adding leaching liquid into said leaching device for replenishing leaching liquid losses caused primarily by said removal step.

4. The method of claim 3, wherein said replenishing leaching liquid is added as a continuous flow of leaching liquid.

5. The method of claim 3, wherein said replenishing leaching liquid is added in batches of leaching liquid.

6. The method of claim 1, further comprising removing said non-soluble heavy metal sulfides from said leaching circuit upon reaching a given quantity or concentration.

7. The method of claim 1, wherein said withdrawing of said bio-gas involves transferring said bio-gas from said solid bed reactor into a low pressure container.

8. The method of claim 1, wherein primarily water is used as said leaching liquid.

9. The method of claim 1, wherein said precipitating is caused by bacterial formation of sulfide from hydrolysis of protein or bacterial sulfate reduction to form said non-soluble heavy metal sulfides in said solid bed reactor.

* * * * *